United States Patent [19]

Ellman et al.

[11] Patent Number: 5,342,356

[45] Date of Patent: Aug. 30, 1994

[54] ELECTRICAL COUPLING UNIT FOR ELECTROSURGERY

[76] Inventors: Alan G. Ellman; Jon C. Garito, both of 1135 Railroad Ave., Hewlett, N.Y. 11577

[21] Appl. No.: 984,348

[22] Filed: Dec. 2, 1992

[51] Int. Cl.$^5$ ............................................. A61B 17/39
[52] U.S. Cl. ...................................... 606/32; 606/34; 606/37; 606/42
[58] Field of Search ...................... 606/32–34, 606/39–42, 13–16, 31; 439/188, 502, 511, 909; 200/302.1, 570, 11 J, 11 R; 128/709, 421–423

[56] References Cited

U.S. PATENT DOCUMENTS

| | | | |
|---|---|---|---|
| 3,286,047 | 11/1966 | Heide | 200/302.1 |
| 4,121,575 | 10/1978 | Mills et al. | 128/709 |
| 4,463,759 | 8/1984 | Garito et al. | 606/42 |
| 4,722,337 | 2/1988 | Losch et al. | 606/16 |

*Primary Examiner*—Stephen C. Pellegrino
*Assistant Examiner*—M. Peffley

[57] ABSTRACT

An electrical coupling unit for electrically connecting an outlet of non-sterile electrosurgical apparatus to a sterile electrosurgical handpiece. The coupling unit is sterile, and can be provided at a location convenient to the surgeon. The coupling unit is also provided with plural outputs for connecting by one or more suitable cables to handpieces held by the surgeon. The latter cables are preferably also maintained in a sterile condition. The coupling unit is provided with a selector switch which functions to selectively connect an output of the electrosurgical apparatus to an output on the coupling unit. The coupling unit outputs are color-coded for ease of selection, each different color representing a different electrosurgical current or instrument. Preferably, the switch knob is also color-coded so that a position representing a particular electrosurgical current or instrument can easily and quickly be achieved. Where multiple cables connected to multiple handpieces are used, it is preferred for the cables also to be color-coded to match the color-coding on the switch.

8 Claims, 4 Drawing Sheets

ELECTRICAL COUPLING UNIT FOR ELECTROSURGERY

This invention relates to electrical coupling units, and in particular sterile electrical coupling unit for coupling currents from non-sterile electrosurgical apparatus to sterile electrosurgical handpiece.

BACKGROUND OF THE INVENTION

In an operating room environment, where a surgeon is to perform a procedure involving use of an electrosurgical apparatus, a problem arises of maintaining sterile procedures in the use of such apparatus. Some electrosurgical apparatus contain a single electrical outlet for providing by cable electrosurgical currents to a handpiece held by the surgeon, The handpiece is sterile but the electrosurgical apparatus is not sterile. If it becomes necessary to change the instrument in the course of the procedure, then the surgeon is unable to make the change because he or she is not allowed to touch any non-sterile objects, Hence, an assistant, who does not have to maintain sterile conditions, must be present to, for example, remove the handpiece and cable from the outlet at the electrosurgical apparatus and plug in a different handpiece and cable under the supervision of the surgeon to make sure that the proper instrument and current has been selected. This can cause problems, as well as undesirable delays.

SUMMARY OF THE INVENTION

An object of the invention is to provide means for allowing the sterile surgeon or a sterile assistant to connect different sterile electrosurgical handpieces to the same outlet of non-sterile electrosurgical apparatus while maintaining sterile conditions.

According to one aspect of the invention, an electrical coupling unit is provided for electrically connecting an outlet of electrosurgical apparatus to an electrosurgical handpiece. The coupling unit is sterile, and can be provided at a location convenient to the surgeon. The coupling unit is provided with an input for connecting by a suitable cable to an outlet of the electrosurgical apparatus. Multiple electrosurgical currents can be made available at the coupling unit by manipulating a control on the apparatus. The coupling unit is also provided with plural outputs for connecting by one or more suitable cables to handpieces held by the surgeon. The latter cables are preferably also maintained in a sterile condition. Hence, the sterile surgeon can directly make the necessary cable change to the coupling unit without imperiling his or her sterile condition.

In accordance with another aspect of the invention, the coupling unit is provided with a selector switch which functions to selectively connect an output of the electrosurgical apparatus to an output on the coupling unit. In this case, the electrosurgical current change can be effected by operating the switch.

In accordance with still another aspect of the invention, the coupling unit outputs are color-coded for ease of selection, each different color representing a different electrosurgical current or instrument. Preferably, the switch knob is also color-coded, so that a position representing a particular electrosurgical current or instrument can easily and quickly be achieved. Where multiple cables connected to multiple handpieces are used, it is preferred for the cables also to be color-coded to match the color-coding on the switch. In this embodiment, the different cables connected to different handpieces holding different instruments can be continuously connected to the coupling unit outputs, and any instrument can be selectively activated by simply operating the switch knob.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

Figure 1:
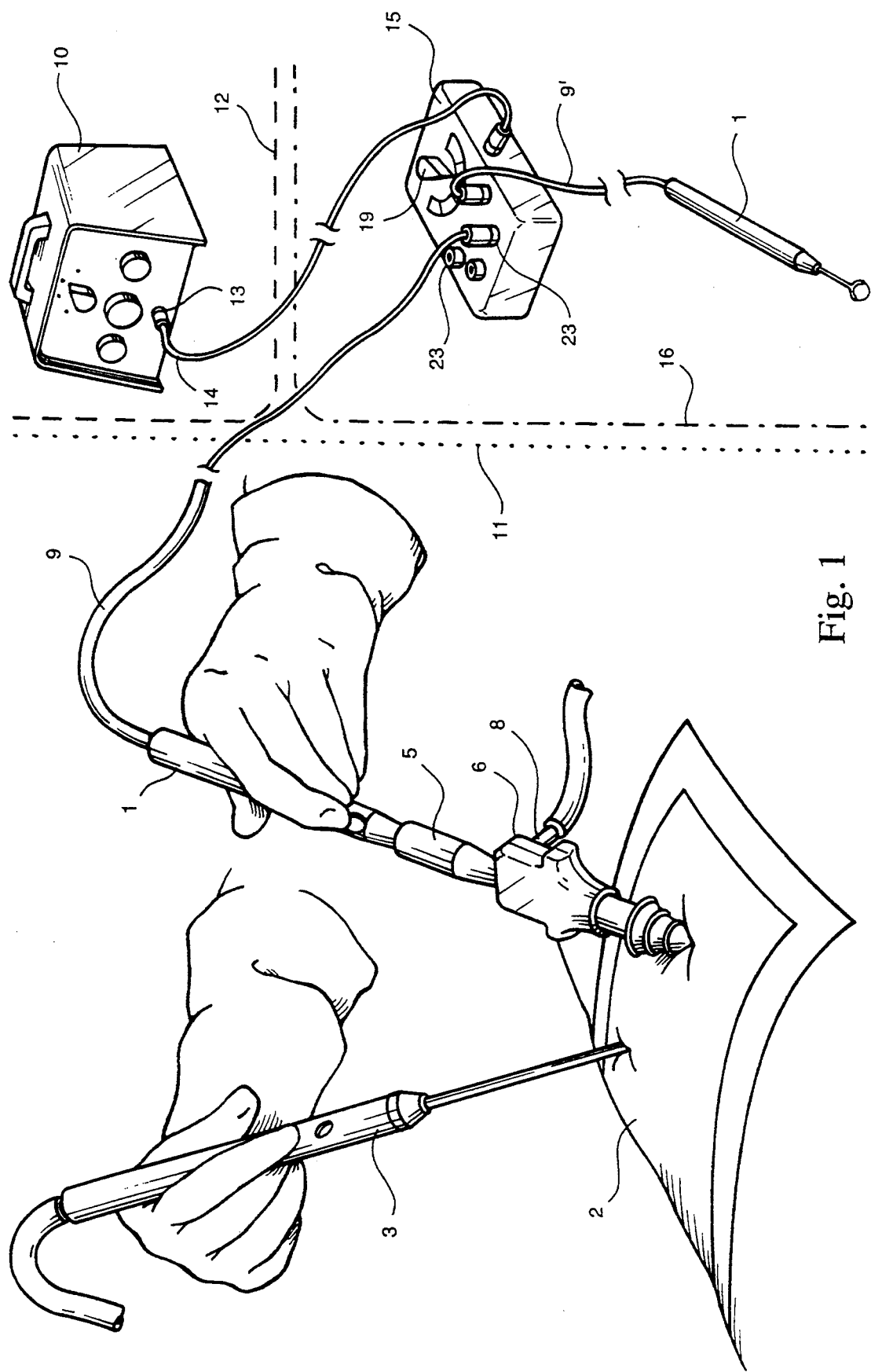
FIG. 1 is a perspective view illustrating use of the coupling unit according to the invention in a typical operating room environment.

FIG. 1 illustrates a typical known surgical procedure involving Minimally Incision Surgery (MIS). Part of a patient's abdomen is shown at 2, with a viewing tube 3 connected to a video monitor (not shown), and with a laparoscopy electrode 5 shown protruding from a conventional trocar 6 also embedded in the patient's abdomen. The trocar 6 has a bore sealable by means of a gasket when the electrode 5 is passed through the trocar bore into the abdomen. For this purpose, the trocar gasket has a given size to accommodate a given size of electrode. A 10 mm size is quite common. Typically air is pumped through the trocar via a valve 8 from an external source to expand the abdomen to afford the surgeon more room in which to work, and the seal serves to limit escaping air. The end of the electrode 5 is connected to a conventional electrosurgical handpiece 1 connected by a cable 9 to a conventional electrosurgical apparatus 10 via a coupling unit 15 according to the invention.

Assuming that the coupling unit 15 was not present and the cable 9 was plugged directly into the output 13 of the electrosurgical apparatus 10, the surgeon during the surgical procedure would be in a sterile condition and the instruments (electrodes) he used, including their handpieces 1, would also be in a sterile condition. That sterile environment is located within the boundaries indicated by the dotted lines 11. Normally, the electrosurgical apparatus is non-sterile, because of the difficulties involved in placing it in a sterile condition. The non-sterile environment is located within the boundaries indicated by the dashed lines 12. Hence, when the surgeon desires to change instruments during the procedure, a non-sterile assistant must remove the cable 14 from the non-sterile apparatus and replace it with a different cable connected to a different instrument.

The invention avoids this delaying action and potential troubles if the assistant choses the wrong cable by supplying a coupling unit 15 between the electrosurgical apparatus 10 and the handpiece 1. The coupling unit 15, having few components and being of small size, can readily be sterilized using known gas sterilization techniques. Alternatively, since the manufacturing cost is small, the coupling unit according to the invention can be delivered in a disposable sterile package to the surgeon and after one use disposed of. In use, therefore, the coupling unit 15 is also located within the sterile environment, indicated by the dash-dot lines 16. Hence, the surgeon is free to touch and manipulate the controls and the connections on the coupling unit without fear of impairing his sterile condition.

Figure 2:
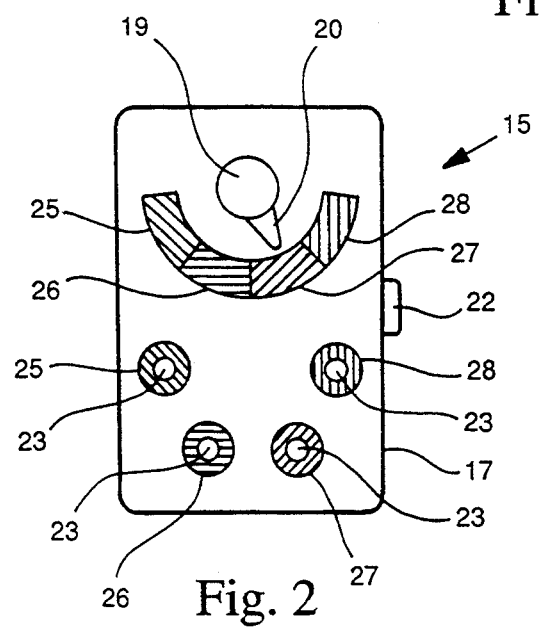
FIG. 2 is a plan view of the coupling unit shown in FIG. 1.

FIG. 2 shows a plan view of the coupling unit of FIG. 1, which comprises a small box 17, for example of plastic, containing on its interior a switch 18 actuable by a control member in the form of a knob 19 with pointer 20. The box 17 supports at the side an input connector in the form of a jack 22, and on top four output connectors also in the form of jacks 23. Located underneath the pointer 20 are four color-coded regions 25-28, each differently colored. The different colors are indicated by the shading. Around each jack 23 is also a color-coded region, also indicated by the same set of reference numerals 25-28, it being understood that the regions with the same reference numeral have the same or matching colors.

Figure 3:
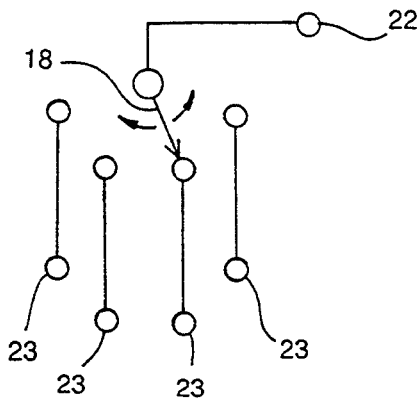
FIG. 3 shows one form of electrical circuit for the coupling unit according to the invention.

The circuitry is illustrated in FIG. 3. The connector 22 is connected to the common terminal of the switch 18, which by rotation can be connected in turn to each of the output connectors 23. In the position shown in FIG. 2, the pointer 20 shows a switch position pointing to color region 27, which means that the connector the second from the right shown in FIG. 3 is connected by the variable arm of the switch to the common terminal and thus to the input connector 22. By plugging the plug end of a conventional handpiece cable (9 in FIG. 1) into the connected jack 23, the handpiece can be made active electrically when the electrosurgical apparatus is switched on.

In the preferred arrangement, the input connector of the coupling unit 15 is a single conductor cable. Different currents are chosen by manipulating controls on the machine 10. Different instruments are chosen by plugging different cable-connected instruments into the multiple outputs. Color-coding the cables avoids mistakes in instruments. Operation of the sterile control 19 by the surgeon ensures the correct choice.

Figure 1A:
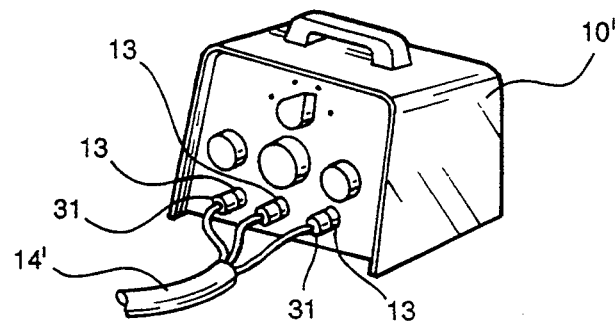
Figure 4:
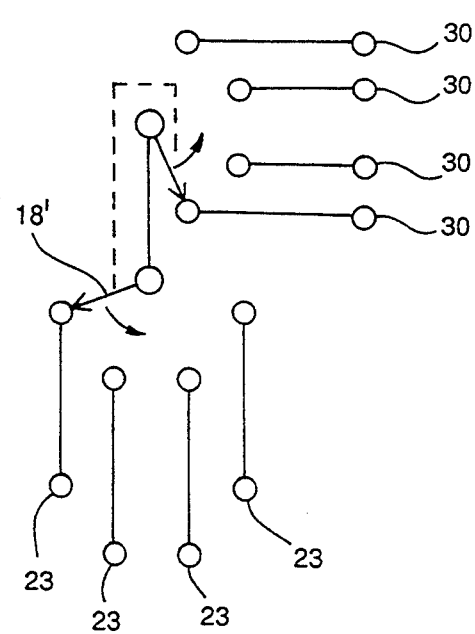
FIG. 4 shows another form of electrical circuit for the coupling unit according to the invention.

In another arrangement, the input is a multi-conductor connector as indicated at 30 in FIG. 4. With different electrosurgical apparatus 10' which has multiple outputs 13 as shown in FIG. 1A, the cable 14' has plural plugs 31 for plugging into plural connectors so that multiple currents are available at each of the coupling unit inputs 30. In this modification, the switch 18' has two ganged arms sc that movement of the switch control 19 to select a particular output 23 also simultaneously switches to a different input 30. Thus, the surgeon by manipulating the control knob 19 of the sterile coupling unit 15 can directly chose the current needed for the surgical procedure contemplated.

In the preferred way of using the coupling unit with the circuitry of FIG. 3 according to the invention, plural cables are provided continuously connected to two or more of the outputs 23. FIG. 1 shows two cables 9 and 9' each with its own handpiece that may be connected to a different electrode. Preferably, the cables are color-coded to match the color 25-28 of the connected jack 23. Preferably, these cables 9, 9' are also sterile. Then, the surgeon can directly activate any electrode via the cable connected to its handpiece 1 by switching the control 19 to point to the proper jack 23. In the embodiment illustrated with 4 outputs 23, 4 separate instruments can thus be connected and selected by operation of control 19.

Figure 5:
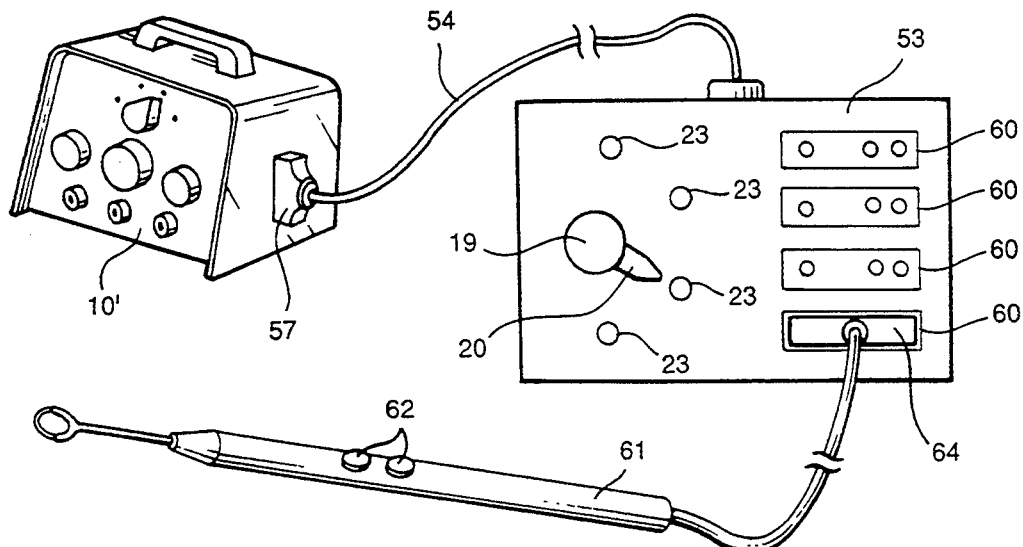
FIG. 5 shows a modified coupling unit according to the invention connected to electrosurgical apparatus and a handpiece.
Figure 6:
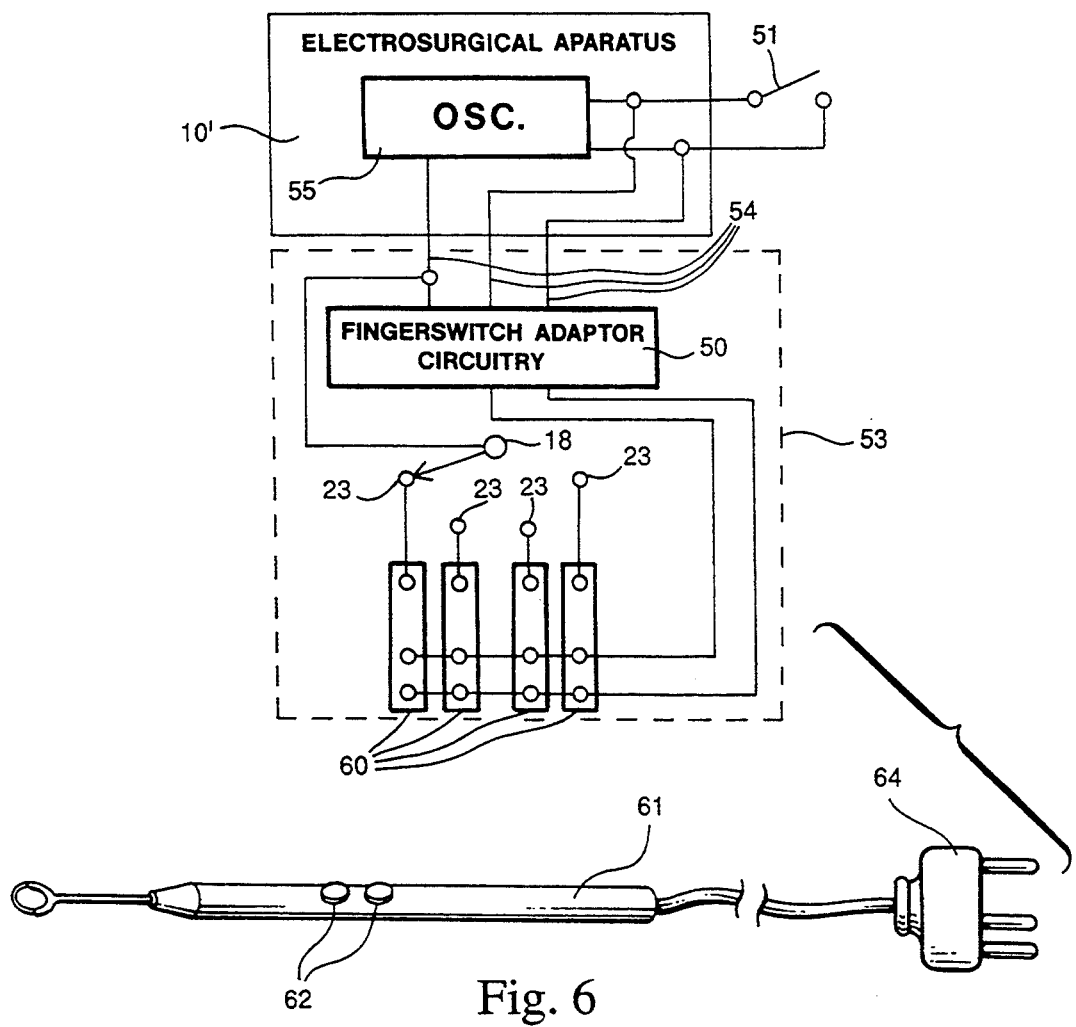
FIG. 6 shows one form of electrical circuitry for the coupling unit of FIG. 5.

FIGS. 5 and 6 show a further modification which combines the circuitry described in our earlier U.S. Pat. No. 4,463,759 with that described above. In the patent, an adaptor 50 is provided to enable the user to activate the electrosurgical apparatus 10' with either a foot control switch 51 or a fingerswitch 62 on the handpiece. This unit, which is commercially available from the Ellmen company of Hewlett, N.Y., plugs into a 3-hole female connector (not shown) on the side of a conventional Ellman electrosurgical apparatus. The handpiece with cable terminates in a 3-prong connector which plugs into the adaptor unit, which is clearly explained in the referenced patent whose contents are hereby incorporated by reference. In its application to the present invention, the adaptor circuitry, illustrated at 50 in the patent drawings, is incorporated into the coupling unit box enclosure 53, As in the patent, the inputs to the adaptor unit are three wires shown at 54 in FIG. 6. These are connected as explained in the patent to the oscillator 55 in the apparatus 10. In this case, a 3-prong connector 57 on the cable 54 providing the three connections is plugged into the 3-jack connector (not shown) on the machine's side. The box 53 contains the same switch 18, control knob 19 and pointer 20 as in FIGS. 2 and 3, connected in the same way to plural outputs 23. In addition, next to each output jack 23 is located a 3-hole connector 60, which corresponds to the output connector for the adaptor of the patent, In the usual way, a conventional handpiece 61 provided with finger switches 62 can by way of a 3-prong plug 64 be plugged into one of the 3-hole sockets 60 to thereby select a desired current in the same way as described earlier when the control knob 19 is rotated to point to the connected socket 60. As with the other embodiments, further simplification is possible by providing color-coded regions for the various pointer positions, and matching color-coded regions adjacent each of the outputs 23 and sockets 60.

It will be further understood that in the FIG. 5 embodiment, the individual outputs 23 can be omitted leaving only the 3-hole sockets as coupling unit outputs.

Figure 7:
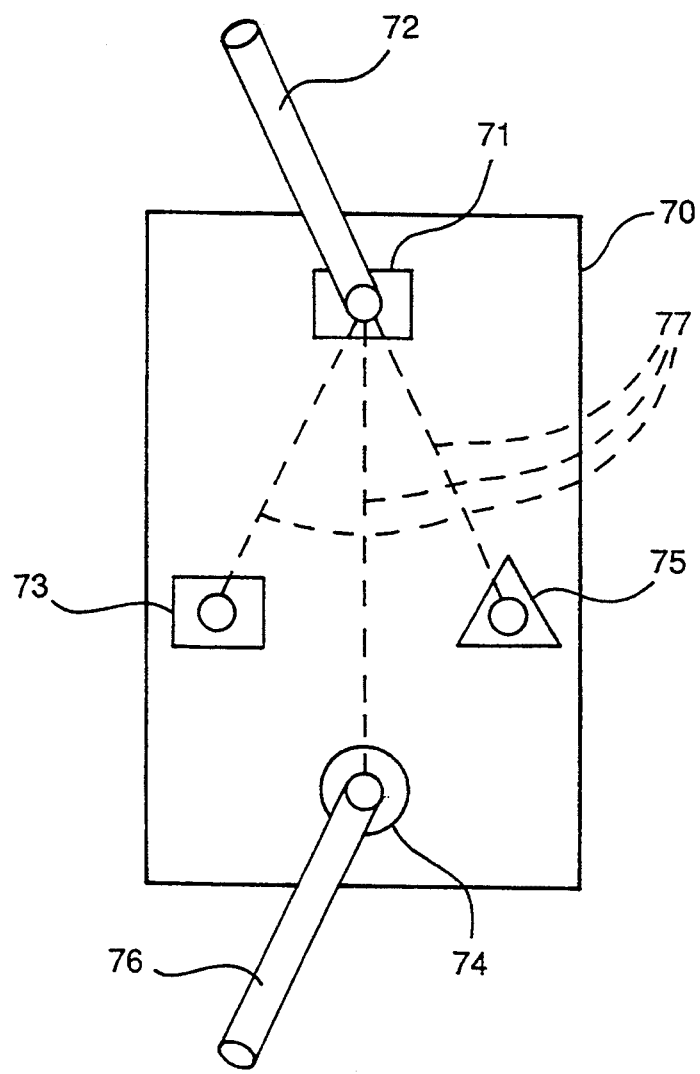
FIG. 7 shows a modified coupling unit in accordance with the invention.

The preferred coupling unit comprise a switch so that the output cables can be permanently plugged in to the unit. A simpler arrangment without a switch is illustrated in FIG. 7. The coupling unit 70 comprises a box as before except that the input connector 71 is on top with a cable 72 from the electrosurgery machine plugged in. Three output connectors 73-75 are shown each to accommodate a banana type plug or the like connected to a cable 76 connected to a handpiece. In this modification, the three output connectors 73-75 are internally 77 connected in parallel to the input connector 71, so only one cable 76 at a time should be plugged in to one of The output connectors. Also, in this modification, instead of color-coding of the outputs, or together with color-coding, the output connectors are differently configured so that they can be selected by touch or feel. This feature can be added to the other modifications also. If desired, the cable ends can also be similarly configured to match that of the connectors. While various configurations would be suitable, three preferred ones are shown: a square or rectangular configuration for connector 73; a circular configuration for connector 74; a triangular configuration for connector 75. As a further alternative, the three output connectors can be reduced to a single connector. In all cases, the control box 70 would be sterile as well as the cables 72, 76 connected to the box. It will also be appreciated that the connectors to receive the plugs can also be of different sizes to match those provided by different manufacturers of handpieces and machines. Thus in the FIG. 7 embodiment, the connectors can be of different sizes to accommodate handpieces of different suppliers.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. In combination:
   (a) non-sterile electrosurgical apparatus having an output,
   (b) a sterile coupling unit having an input and plural connectors outputs,
   (c) a sterile electrosurgical handpiece,
   (d) a first cable connecting the electrosurgical apparatus output to the coupling unit's input,
   (e) a second cable connecting a coupling unit output to the electrosurgical handpiece,
   (f) means on the coupling unit for selectively connecting an input to one of its outputs.

2. The combination of claim 1, wherein said second cable is sterile.

3. The combination of claim 1, wherein said first cable is sterile.

4. The combination of claim 1, wherein said outputs on said coupling unit are plug-in connectors and are color-coded.

5. The combination of claim 4, wherein said second cable is color-coded.

6. The combination of claim 1, wherein the enclosure outputs are differently shaped.

7. The combination of claim 1, further comprising plural handpieces each having to its own second cable, each said second cable being removably connected to a different coupling unit output.

8. The combination of claim 1, wherein said electrosurgical apparatus has plural outputs, said coupling unit has plural inputs, said switch when operated connecting each of the coupling unit inputs to a different coupling unit output.

* * * * *